(12) United States Patent
Coolens et al.

(10) Patent No.: US 8,895,912 B2
(45) Date of Patent: Nov. 25, 2014

(54) PHANTOM FOR CONTRAST IMAGING CALIBRATION

(75) Inventors: Catherine Coolens, Toronto (CA); Harald Keller, Toronto (CA)

(73) Assignee: University Health Network, Toronto (CA)

( * ) Notice: Subject to any disclaimer, the term of this patent is extended or adjusted under 35 U.S.C. 154(b) by 161 days.

(21) Appl. No.: 13/320,385

(22) PCT Filed: May 7, 2010

(86) PCT No.: PCT/CA2010/000721
§ 371 (c)(1),
(2), (4) Date: Jan. 26, 2012

(87) PCT Pub. No.: WO2010/130040
PCT Pub. Date: Nov. 18, 2010

(65) Prior Publication Data
US 2012/0128132 A1    May 24, 2012

Related U.S. Application Data

(60) Provisional application No. 61/178,262, filed on May 14, 2009, provisional application No. 61/249,669, filed on Oct. 8, 2009.

(51) Int. Cl.
*G01D 18/00*    (2006.01)
*A61B 6/00*    (2006.01)
*A61B 6/03*    (2006.01)

(52) U.S. Cl.
CPC .. *A61B 6/583* (2013.01); *A61B 6/03* (2013.01)
USPC ...................................................... 250/252.1

(58) Field of Classification Search
CPC ................... A61B 6/583; A61B 6/032; A61B 2017/00725; A61B 2017/00707; A61B 2560/0228; A61B 6/582; A61B 6/585; A61B 8/4444
USPC ...................................................... 250/252.1
See application file for complete search history.

(56) References Cited

U.S. PATENT DOCUMENTS 4,922,915 A * 5/1990 Arnold et al. ................. 382/128
4,962,514 A * 10/1990 Hart et al. ....................... 378/18

(Continued)

FOREIGN PATENT DOCUMENTS

| WO | 2005018456 A1 | 3/2005 |
| WO | 2007/081662 A2 | 7/2007 |
| WO | 2008/151202 A2 | 12/2008 |

OTHER PUBLICATIONS

International Search Report issued in PCT/CA2010/000721 on Aug. 16, 2010 (3 pp.).

(Continued)

*Primary Examiner* — Marcus Taningco
(74) *Attorney, Agent, or Firm* — Nixon Peabody LLP; David S. Resnick; Leena H. Kartttunen Contarino

(57) ABSTRACT

An imaging phantom for contrast imaging calibration. The phantom includes a body defining at least one cavity having a directional configuration corresponding to at least one predetermined direction of motion of the phantom. The phantom also includes at least one imaging capsule configured to match and be contained in the at least one cavity. The imaging capsule comprises a material having an imaging contrast different from that of the body.

16 Claims, 19 Drawing Sheets

(56) References Cited

U.S. PATENT DOCUMENTS

| | | | | |
|---|---|---|---|---|
| 6,493,574 | B1* | 12/2002 | Ehnholm et al. | 600/429 |
| 7,292,721 | B2* | 11/2007 | Arnold | 382/131 |
| 7,667,458 | B2* | 2/2010 | Yoo et al. | 324/308 |
| 7,738,624 | B2* | 6/2010 | Herold et al. | 378/18 |
| 2003/0045803 | A1 | 3/2003 | Acharya et al. | |
| 2004/0228435 | A1* | 11/2004 | Russell | 378/18 |
| 2008/0212859 | A1* | 9/2008 | Da Silva et al. | 382/131 |
| 2009/0072152 | A1* | 3/2009 | Chen et al. | 250/363.03 |

OTHER PUBLICATIONS

Pandharipande, et al, "Perfusion Imaging of the Liver: Current Challenges and Future Goals", Radiology, 2005. 234: pp. 661-673.

K. Miles, "Computed Tomography Measurements of Perfusion in Cancer Therapy", in In Vivo Imaging of Cancer Therapy, A.F.S.a.P. Price, Editor. 2007, pp. 1-343, Humana Press Inc.: Totowa, N.J.

Cao et al, "Liver function after irradiation based on computed tomographic portal vein perfusion imaging", Int. J. Radiat. Oneal. Bioi Phys, 2008. 70 (1): pp. 154-160.

Mori et al, "Preliminary study: Color map of hepatocellular carcinoma using dynamic contrast-enhanced 256-detector row CT", European Journal of Radiology, 2007. 62: pp. 308-310.

Wiemker et al, "Aspects of computer-aided detection (CAD) and voluntary of pulmonary nodules using multislice CT", The British Journal of Radiology, 2005. 78: pp. 46-56.

Stewart et al, "Hepatic perfusion in a tumor model using DCE-CT. an accuracy and precision study", Phys. Med. Bioi., 2008. 53: pp. 4249-4267.

Kamena et al, "Dynamic perfusion CT: Optimizing the temporal resolution for the calculation of perfusion CT parameters in stroke patients", European Journal of Radiology, 2007.64 (1): pp. 111-118.

Lee et al, "Identification of a Coronary-to-Bronchial-Artery Communication With MDCT Shows the Diagnostic Potential of this New Technology", J. Thorac. Imaging, 2007, 22: pp. 274-276.

Basran et al, "Functional CT in lung with a conventional scanner: simulations and sampling considerations", Phys. Med. Biol., 2004. 49: pp. 1755-1771.

Coolens et al, "Implementation and Characterization of a 320-slice volumetric CT scanner for simulation in radiation oncology". Med. Phys., 2009, pp. 5120-5127.

Grosjean et al, "Influence of a longitudinal motion on image quality with a 64-channel CT scanner", Proceeding of the 29th Annual International, Conference of the IEEE EMBS, 2007, pp. 2924-2927.

Shirato et al, "Intrafractional Tumor Motion: Lung and Liver", Seminars in Radiation Oncology, 2004,14 (1): pp. 10-18.

Silverman et al, "Investigation of lung nodule delectability in low-dose 320-slice computed tomography", Med. Phys., 2009.36 (5): pp. 1700-1710.

Keall et al, "Acquiring 4D thoracic CT scans using a multislice helical method", Phys. Med. Bioi., 2003. 49: pp. 2053-2067.

Huda et al, "Technique factors and image quality as functions of patient weight at abdominal CT", Radiology 2000; 217: pp. 430-435.

Miles, K.A., "Perfusion CT for the assessment of tumour vascularity: which protocol?" British J. of Radial 2003; 76, pp. S36-S42.

Miles, K.A., "PQuantitiative contrast-enhanced computed tomography: is there a need for system calibration?" Eur. Radial 2007; 17, pp. 919-926.

Driscoll et al, "Development of a dynamic quality assurance testing protocol for multisite clinical trial DCE-CT accreditation", Med. Phys., 40(8), 2013, pp. 081906-1-081906-14.

Thorndyke et al, "Reducing respiratory motion artifacts in positron emission tomography through retrospective stacking", Med. Phy. 2006, 33, pp. 2632-2641.

* cited by examiner

PHANTOM FOR CONTRAST IMAGING CALIBRATION

CROSS REFERENCE TO RELATED APPLICATIONS

This application is a 35 U.S.C. §371 National Phase Entry Application of International Application No. PCT/CA2010/000721, filed May 7, 2010, which designates the United States, and which claims benefit under 35 U.S.C. §119(e) of the U.S. provisional application No. 61/178,262, filed on May 14, 2009 and U.S. Provisional application No. 61/249,669, filed Oct. 8, 2009, the entireties of which are hereby incorporated by reference.

TECHNICAL FIELD

The present disclosure relates generally to the field of imaging phantoms, in particular phantoms for contrast imaging, for example for calibration of contrast imaging.

BACKGROUND

Motion artifacts typically are a serious issue in perfusion imaging, in particular for dynamic contrast-enhanced (DCE) computed tomography (CT) imaging. The uncertainties of kinetic parameters (e.g. perfusion) may stem from uncertainties in the uptake curve and arterial input function measurement, which is in turn determined by the scanning technique. In addition, there usually is an implicit assumption in CT perfusion studies that the enhancement in Hounsfield unit (HU) measurement in the vasculature and tissues is linearly proportional to their concentration of contrast agent. As long as this relationship is the same for both artery and tumor, the calibration of contrast concentration versus HU typically is not required. Typically, this is rarely the case, especially not in the thoracic region, where beam hardening effects may occur both due to potential contrast in superior vena cava, air/tissue inhomogeneities and differences in patient size [16]. In addition, there is an increasing use of absolute HU thresholds for functional analysis as well as segmentation of tissues of interest. As such it is now recognized that there is a clear need for not only calibrating the CT system for sensitivity to iodine in both relative and absolute terms but also for assessing the stability of the calibration over time [17]. Despite this recognition, there are currently no perfusion- or dynamic contrast calibration phantoms commercially available or discussed in the literature.

Perfusion imaging provides the ability to detect regional and global alterations in organ blood flow [1]. In tumors, an increase in perfusion is typically associated with the process of angiogenesis and this has proven to be related to the staging of disease [2] and treatment response [3].

One possibility to measure tissue perfusion is through the use of dynamic contrast-enhanced (DCE) computed tomography (CT) imaging. With DCE-CT, the redistribution of a contrast agent after a bolus injection can be visualized as a time-sequence. DCE-CT has been extensively developed during the last decade, not least because of enormous progress in computed tomography scanner technology. It may be an attractive imaging modality because of its simplicity of quantification (linearity between injected contrast concentration and CT contrast enhancement) and the possibility to add it to conventional anatomical CT examinations [2].

One potential application of DCE-CT is the measurement of liver and lung perfusion in order to distinguish malignancy from normal tissue and/or fibrosis [4]. However, in order to apply DCE-CT to these or other organs that are subject to breathing motion, motion artifacts should be considered.

Not only may the contrast in the moving organ be subject to reconstruction artifacts, it may also be affected by motion artifacts, such as motion-induced blurring. This may be a ubiquitous and noticeable artifact when imaging respiratory-sensitive organs in free-breathing conditions [5].

For dynamic imaging applications, motion-induced blurring may add temporal variations to the measured contrast enhancement values, which may lead to errors in the quantification and therefore to artifacts of the resulting parametric images. In addition, if the imaging field-of-view is limited, the vessel(s) of interest may periodically move out of the plane of interest resulting in further loss of contrast enhancement sampling.

Reducing these artifacts is not straightforward. DCE-CT imaging of the liver is usually performed under breath hold [4] [6]. In principle, reconstruction artifacts and motion-induced blurring may be minimized with a high-temporal resolution, for example by employing a high scanning frequency [7]. This is becoming feasible with current state-of-the-art multi-detector CT systems that enable a variety of noninvasive techniques with unprecedented spatial and temporal resolution [8]. Often, however, multi-detector scanners are still limited in the field-of-view in cradio-caudal extent which limits the ability to control out-of-plane respiratory motion [9]. The latest developments in CT scanner technology (e.g., Aquilion One, Toshiba, Tochigi Pref., Japan) may offer advantages over conventional CT systems through the capability for volumetric scanning of high speed and increased coverage within a single gantry rotation. Such a 320-slice CT scanner has been used for implementation into routine CT simulation, offering sub-millimeter spatial resolution at cranio-caudal coverage of 160 mm in a single rotation of 0.35 [10]. This volumetric scan mode may be capable of mitigating both the lack of temporal scan resolution as well as limited field-of-view.

A potential drawback of faster acquisition with a large-field-of-view may be a decreased image quality. Therefore, a scanning protocol that includes considerations about image quality and, at the same time, patient dose, may not always employ the fastest gantry rotation time.

Conventional calibration phantoms typically are designed for use only in static conditions, and hence may not be useful when considering motion artifacts. Other phantoms may be designed mainly for quantifying volume changes under motion, rather than for contrast calibration.

BRIEF DESCRIPTION OF THE DRAWINGS

In the following description, reference is made to the accompanying drawings, which form a part hereof, and in which there is shown by way of illustration, examples of the present disclosure. Such examples do not define or limit the scope of the disclosure.

DETAILED DESCRIPTION

Figure 1:
FIG. 1 is a perspective view of an example imaging phantom, in accordance with an example embodiment of the present disclosure.

The imaging phantom presently disclosed may be useful for assessing the impact of motion blurring, for example by allowing for quantifying and modeling the change of contrast enhancement of elongated vessel-like objects under various moving conditions and a range of acquisition parameters for contrast imaging, such as using CT scanner, including a range of gantry rotation times. Such a calibration phantom may be useful for calibrating the accuracy and/or precision of parameter measurements and/or the patient dose for contrast imaging, for example in DCE-CT.

In some aspects, there is provided an imaging phantom for contrast imaging calibration. The phantom includes a body defining at least one cavity. The at least one cavity has a directional configuration corresponding to at least one pre-determined direction of motion of the phantom. In some example embodiments, the phantom includes at least one imaging capsule configured to match and be contained in the at least one cavity. The imaging capsule includes a material having an imaging contrast different from that of the body.

The imaging capsule may be hollow and contain an imaging material, such as a radioactive substance. The imaging capsule may be made of Teflon. Other suitable material for the capsule or that may be contained in a hollow capsule may include high-atomic number materials, such as metals. In some examples, the imaging capsule may be made of a material having a different density than the body of the phantom. For example, the body may be made of a wood material (e.g., to mimic the imaging properties of air) and the imaging capsules may be made of materials to simulate soft tissue or bone tissue.

By "directional configuration" is meant that the cavity has a directional preference—that is, the configuration of the cavity is not uniform in all directions. For example, a spherical configuration is uniform in all directions and thus is not a directional configuration. In contrast, a cylindrical configuration is not uniform in all directions (e.g., it has a longitudinal axis and a transverse axis, and is longer along its longitudinal axis than along its transverse axis) and thus is a directional configuration. Other directional configurations include, for example, cubic configurations, rectangular configurations and other polygonal, non-polygonal or irregular configurations.

The cavity and capsule may be any size suitable for the intended use of the phantom. For example, for a CT scanner, the cavity and capsule may have a diameter in the range of about 0.5 mm to about 1 mm, while for a PET scanner, the cavity and capsule may have a diameter in the range of about 3 mm to about 5 mm. The cavity may have any suitable orientation to correspond to a pre-determined direction of motion.

In some example embodiments, the directional configuration of the at least one cavity is a cylindrical configuration having a longitudinal axis. In some examples, the longitudinal axis of the cylindrical configuration corresponds to the at least one pre-determined direction of motion in one of: a parallel alignment, a perpendicular alignment, and a skewed alignment.

In some example embodiments, the body of the phantom defines a plurality of cavities. At least two of the plurality of cavities have directional configurations respectively corresponding to at least two different pre-determined directions of motion of the phantom. There is a corresponding plurality of capsules, each configured to match and be contained in a respective cavity. In some examples, the plurality of cavities has respective directional configurations corresponding to at least three different pre-determined directions of motion of the phantom. This may help to provide a basic level of confidence in the calibration using the phantom. In some examples, a greater number of cavities and corresponding capsules may provide greater accuracy and/or confidence level in calibration. The number of cavities and the configuration of the cavities may be dependent on the type of calibration and/or the imaging modality intended for the phantom.

In some examples, at least two of the cavities may have different dimensions or sizes. There may be a corresponding plurality of differently-sized capsules, each configured to match and be contained in a respective cavity. This may be useful for calibrating for spatial resolution and/or partial volume effects.

In some aspects, there is provided a combination for contrast imaging calibration, the combination including the phantom described above and a motion device. The motion device is operable for moving the phantom in the at least one pre-determined direction of motion. For example, the motion device may be a motorized device, such as the Modus™ motion device.

In some example embodiments, the motion device is operable for moving the phantom in a plurality of pre-determined directions of motion. In some examples, the plurality of pre-determined directions of motion defines an open or a closed motion path in three-dimensional space.

EXAMPLES

An example imaging phantom is shown in FIG. 1. In this example, the phantom includes an acrylic cylinder defining 12 cavities for containing 12 capsules of fixed 20 mm length, and varying diameters (e.g., 1, 2, 5 and 10 mm) and orientations (e.g., longitudinal, diagonal and axial) at predefined positions. The phantom is shown with the two halves of its body unassembled, to expose the cavities within. As shown in this example, the cavities are defined with complementary depressions in each half of the body.

The phantom may be used under both static and moving conditions. In this example, the orientations of the cavities were defined with respect to the plane defined by the rotating gantry of the CT scanner: for example, a cavity in the longitudinal orientation was oriented with its long axis perpendicular to the gantry (i.e., perpendicular to the direction of motion), whereas a cavity oriented axially was oriented with its long axis in the plane of the gantry (i.e., parallel to the direction of motion). The diagonal orientation denotes a cavity axis drawing an angle of 45° with respect to the plane of the gantry (i.e., skewed to the direction of motion), assuming that this angle is an average angle of rotation of the blood vessels with respect to this plane. In the example shown in FIG. 1, there are four axially oriented cavities having diameters of 1, 2, 5 and 10 mm (indicated as A1, A2, A5 and A10, respectively); there are four diagonally oriented cavities having diameters of 1, 2, 5 and 10 mm (indicated as D1, D2, D5 and D10, respectively); and there are four longitudinally oriented cavities having diameters of 1, 2, 5 and 10 mm (indicated as L1, L2, L5 and L10, respectively).

Figure 12:
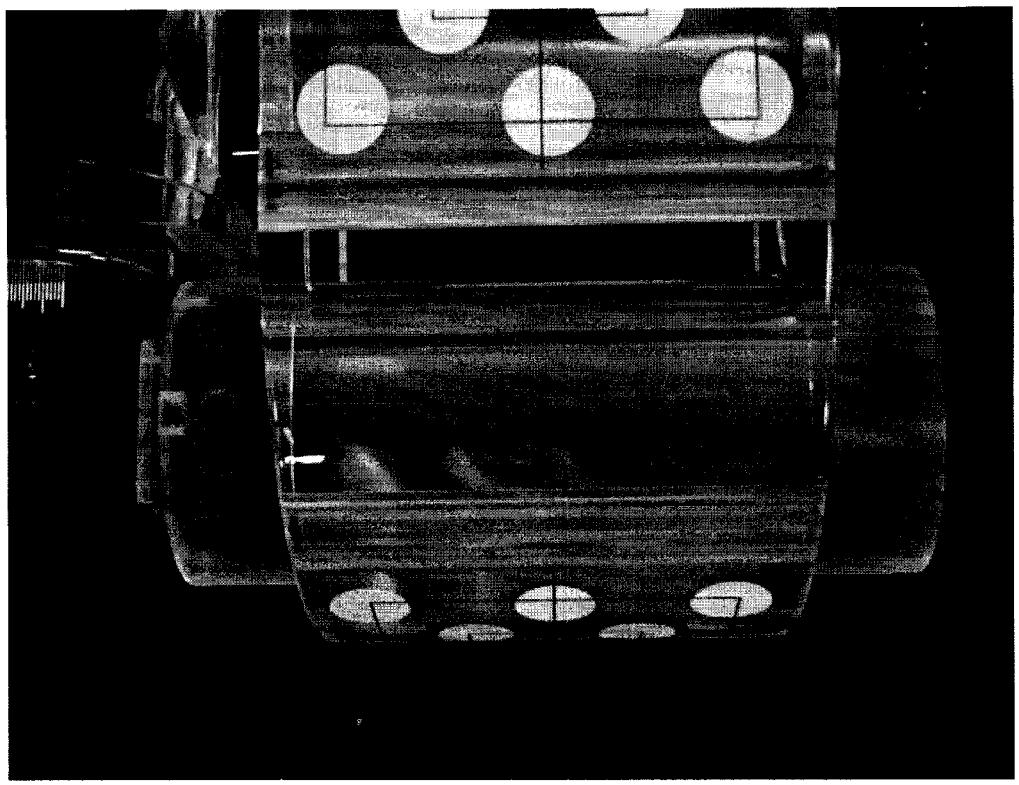
FIG. 12 shows a perspective view of the phantom of FIG. 1 with an example motion device.
Figure 13:
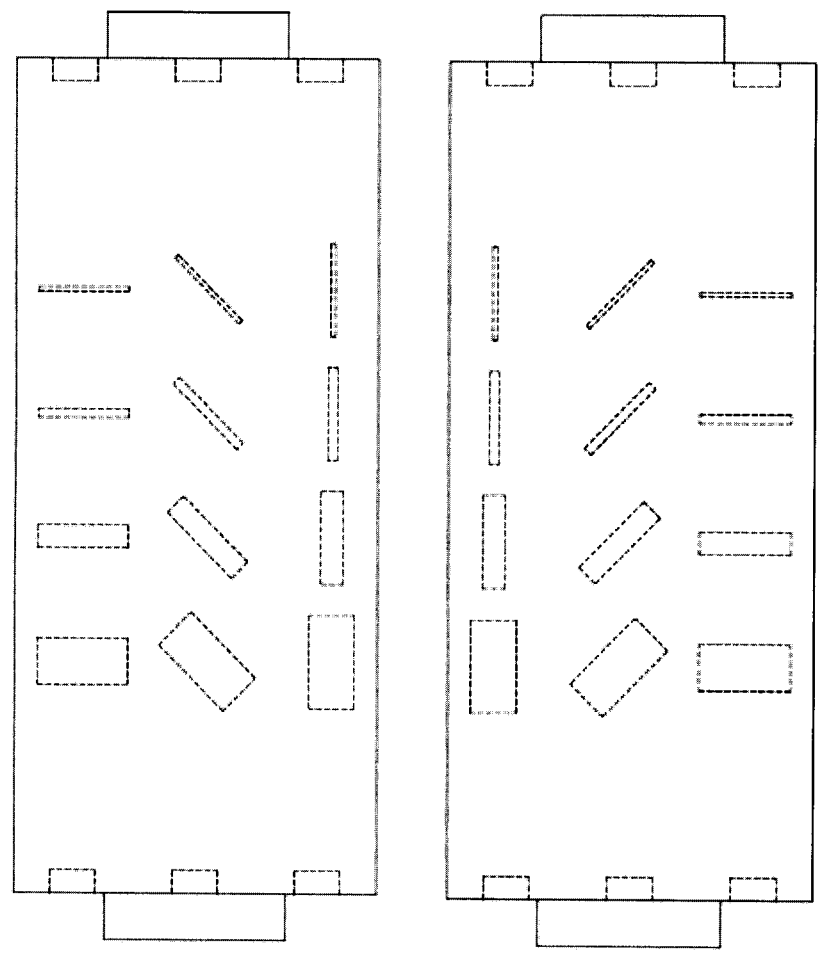
FIG. 13 shows a front view of the phantom of FIG. 1.
Figure 14:
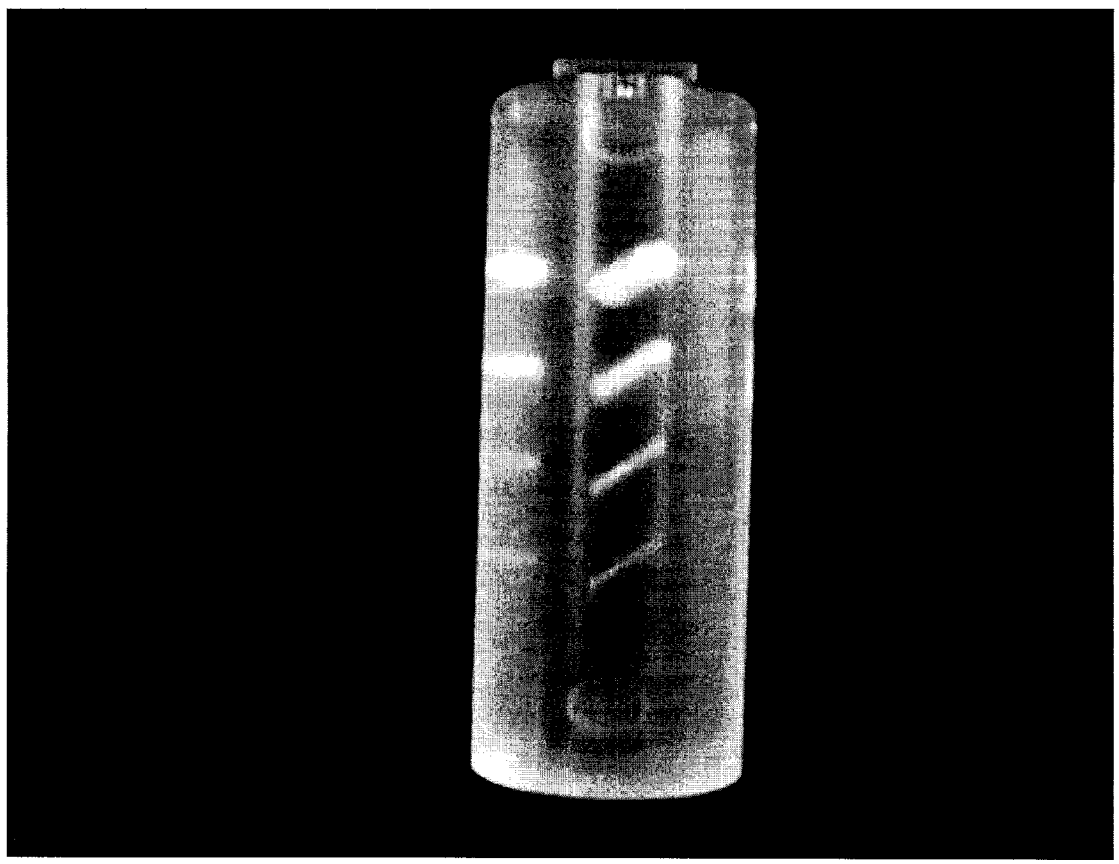
FIG. 14 shows a front view of the phantom of FIG. 1 with two sides assembled.
Figure 15:
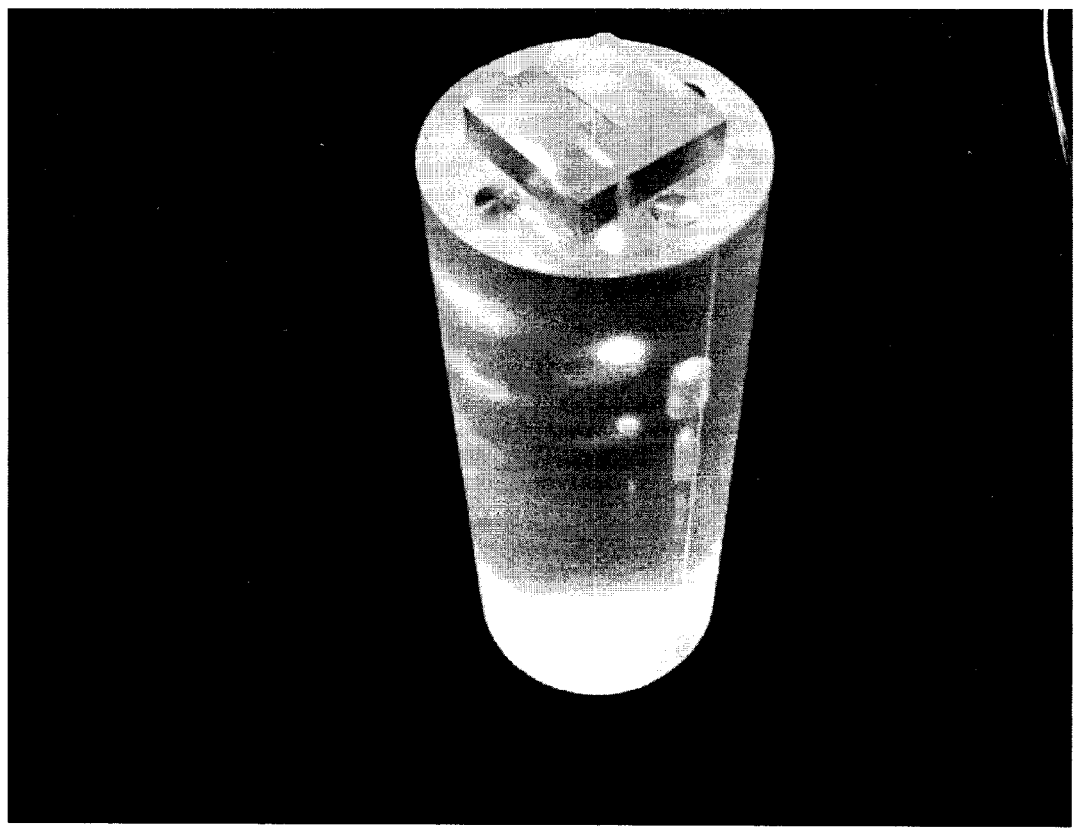
FIG. 15 shows a top perspective view of the assembled phantom of FIG. 14.
Figure 16A:
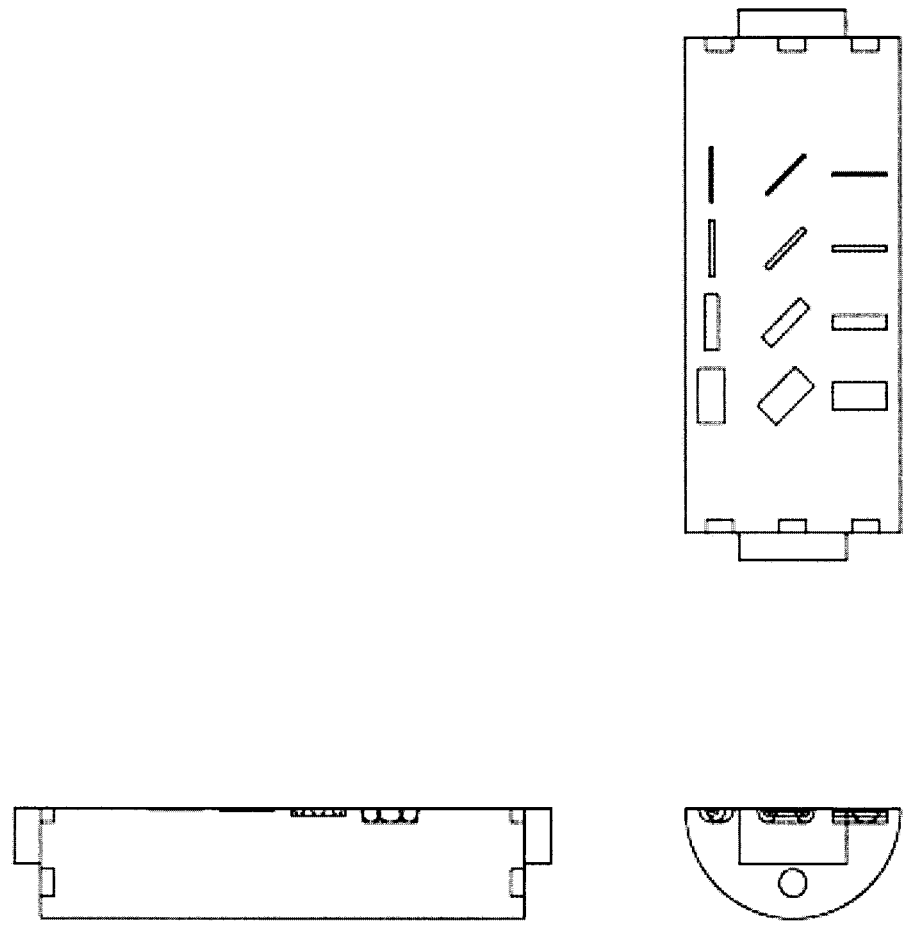
FIGS. 16A and 16B show two-dimensional views of a first side and a second side of the phantom of FIG. 1.
Figure 16B:
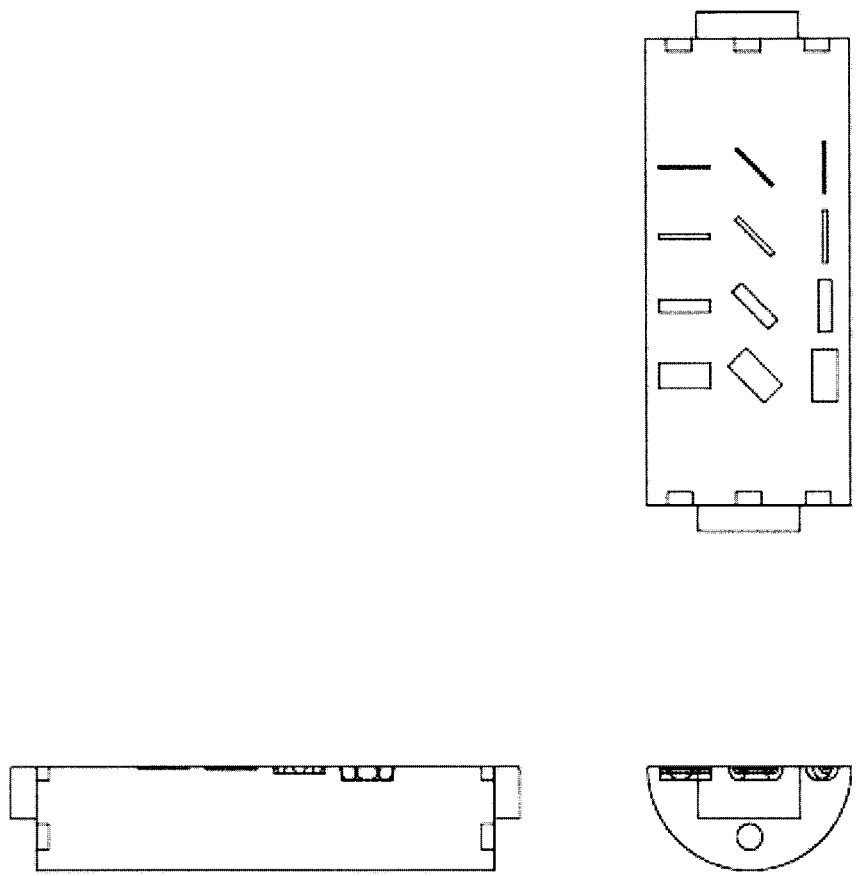
Figure 17A:
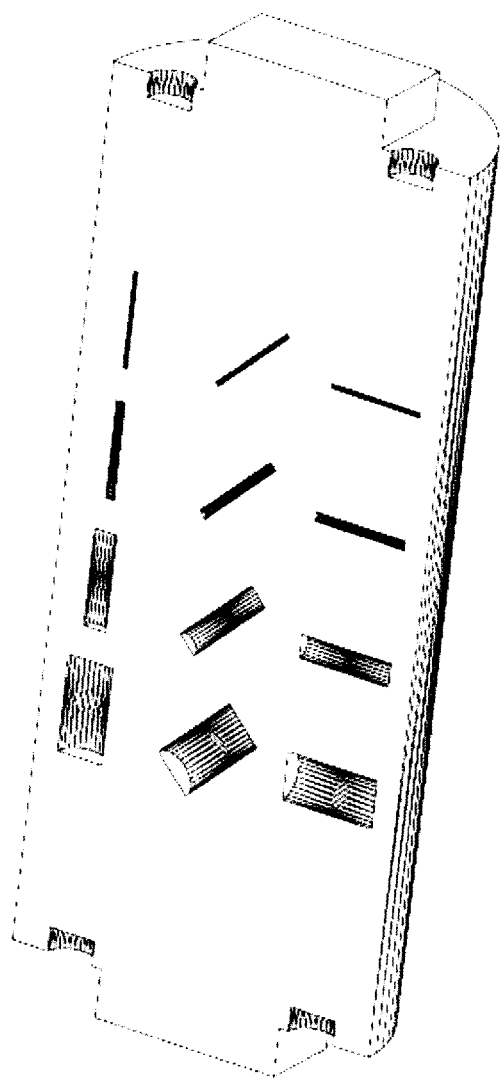
FIGS. 17A and 17B show perspective views of the first side and the second side of the phantom of FIG. 1.
Figure 17B:
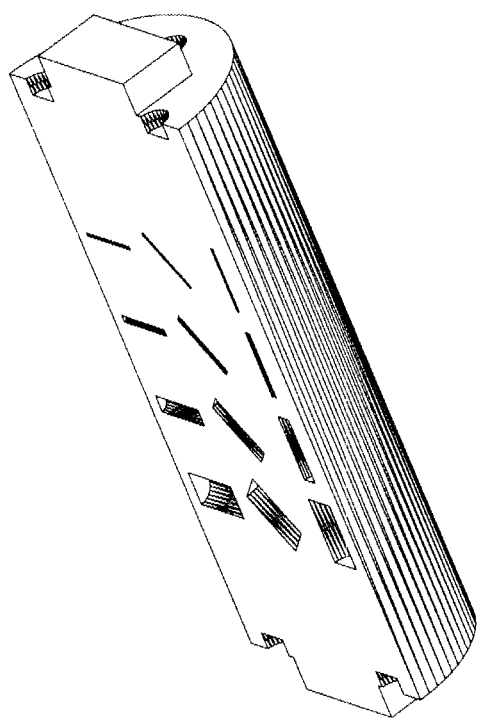

FIG. 12 shows a perspective view of the example phantom with an example motion device (in this example, the Modus™ respiratory motion platform). FIG. 13 shows a front view of the example phantom. FIG. 14 shows a front view of the example phantom with two sides assembled. FIG. 15 shows a top perspective view of the assembled example phantom. FIGS. 16A and 16B show two-dimensional view of first and second sides of the example phantom. FIGS. 17A and 17B show perspective views of the first and second sides of the example phantom.

Example of Imaging Using Example Phantom

In this example, the capsules contained in the cavities are made of Teflon. Teflon was chosen as the capsule material to mimic a maximal contrast enhancement in the arterial input function of the liver [6].

In this example, the motion device is a motor-driven platform (e.g., Robo Cylinder, IAI Corporation) on a track. The platform drove the phantom along one dimension yielding uniform motion along the longitudinal axis of the scanner. The motion parameters (e.g. direction and speed), in this example, were software controlled which permitted customized positioning and complex temporal motion profiles to be programmed and executed. The direction of motion was towards (i.e., into) the gantry and four different uniform phantom motion speeds of 0 cm/sec (i.e., static condition), and 0.5, 1.0 and 2.0 cm/sec (i.e., moving condition) were investigated. These speeds may represent normal breathing motion during different phases of the breathing cycle. [11] [12]

Image Acquisition

CT imaging was performed on the 320-slice Aquilion ONE scanner (Toshiba, Tochigi Pref., Japan) that is capable of acquiring a 16 cm field-of-view in one rotation using 320 detectors of 0.5 mm thickness ("Volume Mode") [10]. Although a 320-slice CT scanner was used, other types of CT scanners may also be suitable. The large cone-angle collimation allowed all Teflon capsules to be imaged in one rotation. For all except the largest phantom motion speed the capsules remained in the field of view during the time of one gantry rotation ($T_G$). All images were acquired in Volume Mode for a range of gantry rotation times $T_G$, exposures, and phantom speeds (see section II.A.). Images were acquired at a fixed tube voltage of 120 kVp and the tube current was chosen such that a fixed X-ray output of 175 mAs resulted for all different gantry rotation times ($T_G$=0.35, 0.5, 0.75, 1.0, 1.5, 2 and 3 sec). Hence, the tube current was between 60 mA and 500 mA. For the larger motion amplitudes, two volumes were combined axially to cover the whole acrylic cylinder range up to 18 cm. Reconstruction was done at a slice thickness of 0.5 mm resulting in an isotropic voxel size for all acquisitions.

HU Variation with Tube Voltage and Current

In order to test the stability of the acquisition protocol and establish a baseline for contrast enhancement, the variation in measured Hounsfield Units (HU) of the static Teflon capsules was assessed for a range of x-ray tube currents between 50 mA to 400 mA. The behaviour of background HU values to the tube current variation was evaluated by measuring the average HU value over a homogeneous region of interest in the acrylic cylinder outside the capsules.

Image Analysis

All images were exported in DICOM format and read into MATLAB for subsequent analysis of HU accuracy and volume definition. The CT images were analyzed by first identifying identical regions of interest (ROI) around all twelve Teflon capsules. Each ROI was a sphere with a diameter of 22.5 mm, which is 2.5 mm larger than the length of the capsules and was centered about each capsule center. The size of the sphere was therefore large enough to cover the entire capsules in the static condition. For the images of the moving phantom the sizes of these regions of interest were not changed even though the distance of travel of the moving capsules now exceeded the size of the spheres. These circumstances imitate closely the situation for the analysis of an arterial input function where usually a fixed region of interest is chosen as well.

For each spherical ROI, a fixed CT number was selected as a threshold and the mean HU of the voxels both inside the ROIs and with CT numbers exceeding the threshold was computed. The value of the threshold was chosen such that the segmented voxels in the static condition resulted in the correct volume. It was found that a Hounsfield value of 1400 met this condition. This CT threshold value was then kept constant for the entire analysis, in the static and the moving condition.

Motion Model

In order to further analyze the observed changes in contrast enhancement, a simple motion model was developed in order to predict the changes in Teflon HU as a function of phantom motion speed and gantry rotation time. Although a specific model is described here and is used in examples below, the present disclosure is not limited to this model, and it not bound to any theory relied upon or proposed by this model. This motion model is used only for the purpose of illustration and is not intended to be limiting.

In this example, two types of blurring affect the image of the Teflon capsules: the point spread function (PSF) of the CT scanner and the phantom motion, represented by a motion spread function. In order to keep the model as simple as possible, the two kinds of blurring were implemented as two one-dimensional convolutions. The consequence of this design is that only the maximum HU value could be predicted for each capsule. This limitation may be overcome in other models, which may be more complex.

Figure 2:
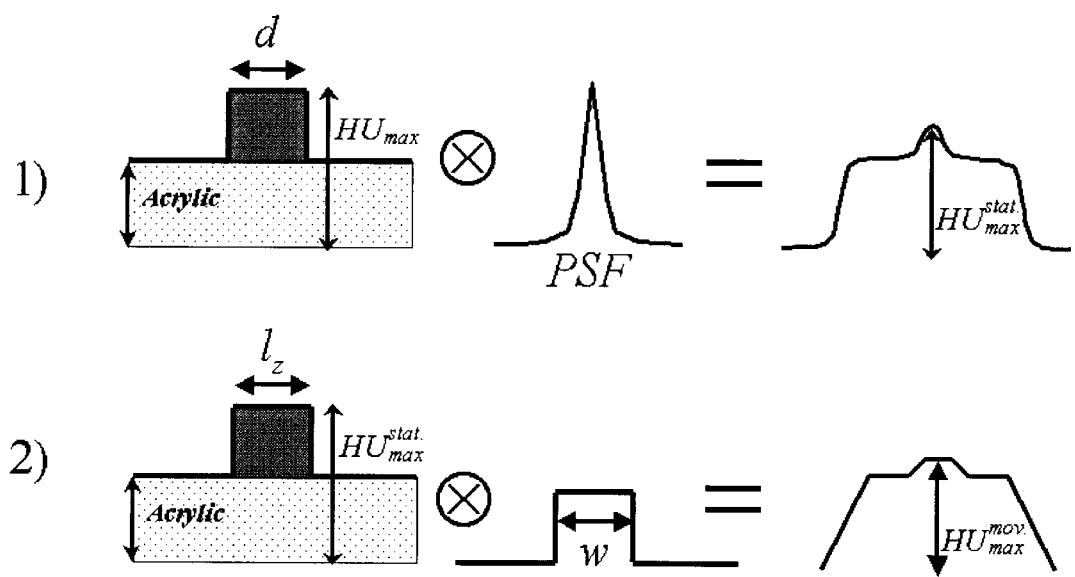
FIG. 2 illustrates an example motion model for prediction of HU.

FIG. 2 illustrates an example motion model for calculating motion artifacts, in this example the effects of PSF and motion blurring on the measured maximum HU value of the capsules. The PSF describes the spatial blurring of the image acquired in the static condition. The modulation transfer function (MTF) of the scanner was measured before [10] [13]. Based on this measured MTF, the PSF of the scanner was computed. This example motion model uses a convolution method for prediction of $HU_{max}^{stat}$ and $HU_{max}^{mov}$.

A plane through the central axis of the cylindrical capsules intersects the capsule in a rectangle of dimensions d and L (i.e., the diameter (d) and the length (L) of the capsules). The shape of a profile through that rectangle along d, in the image slice containing the rectangle, is a rectangular function with a width d and height $HU_{max}$ where $HU_{max}$ is the maximum HU of the largest Teflon capsule.

In the first step of the model this box function was convolved with the normalized PSF of the scanner. The result of this convolution is a function with the maximum height $HU_{max}^{stat}$ equal to the maximum HU value of each capsule in the static condition. As shown in FIG. 2, 1) illustrates the first step convolution of a capsule's rectangular function (above the Acrylic background) with the point spread function (PSF) of the scanner. d is equal to the capsule diameter and $HU_{max}$ is equal to maximum HU value of the capsule in the static mode. $HU_{max}^{stat}$ is the maximum HU value after convolution of the rectangular function with the normalized PSF.

In a second step a profile through the blurred capsule in the direction of motion was convolved with the motion spread function which is a box function of width $w=v_{Ph} \cdot T_G$. This represents the motion blur with $v_{ph}$ is the phantom motion speed and $T_G$ the gantry rotation time. w is the distance of travel (i.e., displacement) of the phantom and capsules during the time of one gantry rotation. In FIG. 2, 2) illustrates the second step convolution of a cross section through the capsule along the direction of motion with the motion spread function. $l_z$ is equal to the capsule dimension in motion direction. w is the travel of the capsule during the time of one gantry rotation. $HU_{max}^{mov}$ is the maximum HU value after convolution with the rectangular normalized motion spread function.

The profile through the capsule along the direction of motion is determined by the height $HU_{max}^{stat}$ of the blurred static profile computed in the first step and the width $l_z$ which is given by d and the orientation (angle θ) of the capsule with respect to the direction of motion: for the longitudinal orientation (θ=0°)$l_z$=L, for the axial orientation (θ=90°)$l_z$=d, and for the diagonal orientation (θ=45°) $l_z$=d/cos θ.

The height of the profile after the second convolution determines $HU_{max}^{mov}$, the maximum HU value for any moving capsule.

Although an example motion model has been described, other motion models may be developed, for example using other phantoms, which may include more complex calculations to take into account specific motion artifacts, using conventional methods.

Results of Example Imaging

HU Variation with Tube Voltage And Current

Figure 3:
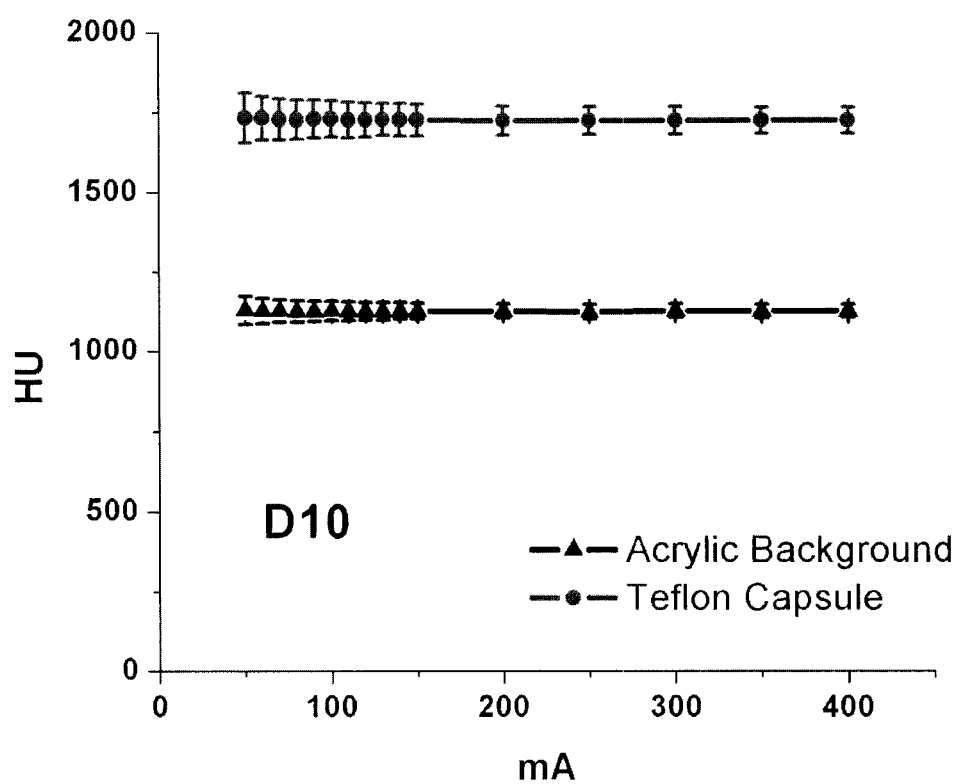
FIG. 3 shows measured HU values for the phantom of FIG. 1, in a static condition.

FIG. 3 shows the variation of measured HU values versus different x-ray tube current of the 10 mm diameter Teflon capsule in diagonal orientation (i.e., D10 indicated in FIG. 1) when the phantom is in the static condition, in this example. The standard deviation of each point (error bar) for the capsule was calculated for the voxels containing HU values above a pre-defined threshold of 1600. The standard deviation of the background was calculated in the homogeneous Acrylic part of the cylinder and for the voxels containing HU values above zero.

It was found that the variation of the measured mean HU values between the lowest and the highest tube current was within 1%. Similar results were obtained for the other capsules (results not shown). The standard deviation of the HU values was computed over the voxels with HU values larger than a fixed threshold of 1600. They decreased with increasing tube current, as expected.

Static Condition

Figure 4:
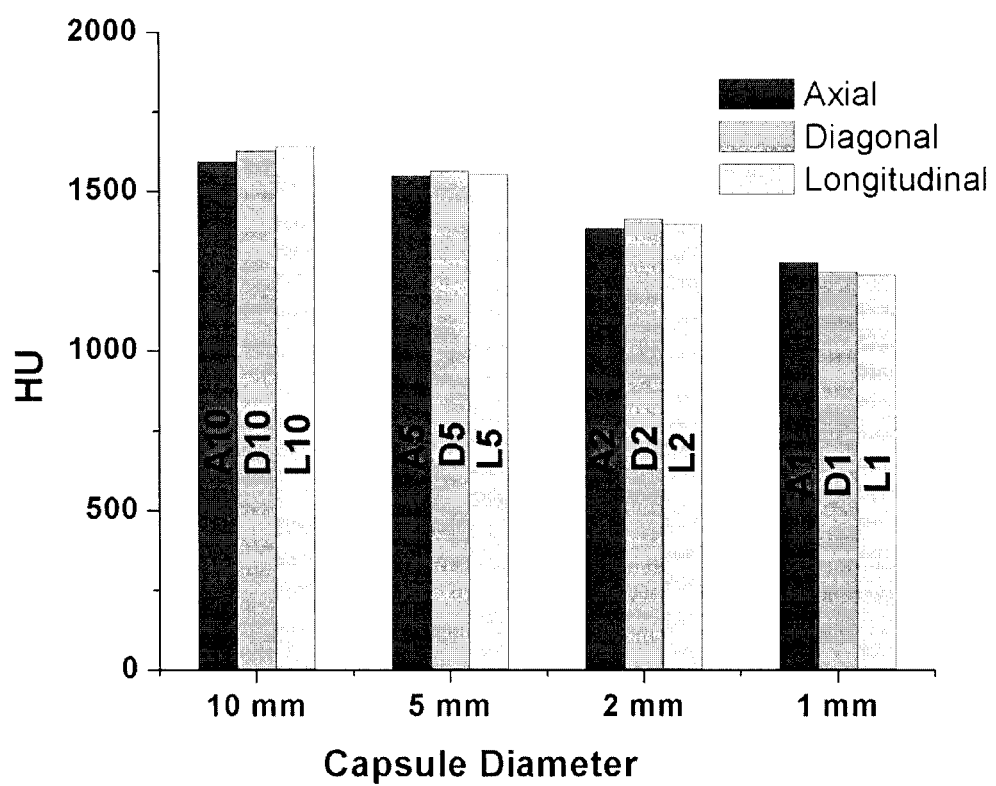
FIG. 4 shows measured HU values for the phantom of FIG. 1 in regions of interest.

FIG. 4 shows the mean HU values in spherical regions of interest around all 12 capsules, versus different capsule diameters, for the static condition, in this example. The three bars for each capsule diameter represent the different capsule orientations. In general, the capsules with larger diameter show larger HU values. The average difference between the HU of the 10 mm capsules and 2 mm capsules is 13.8% and the average HU discrepancy between 10 mm and 1 mm capsules is 22.7%.

Figure 5:
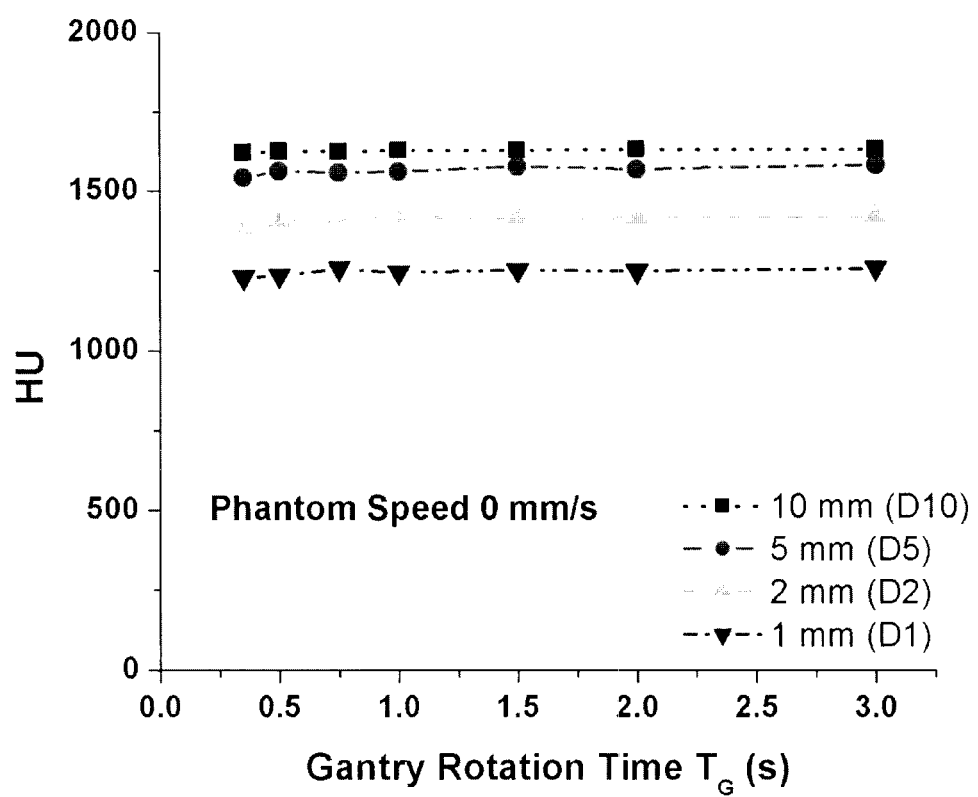
FIG. 5 shows measured HU values of different example capsules in the phantom of FIG. 1.

As expected, HU values are not dependent on gantry rotation time, as demonstrated in FIG. 5 for the diagonal orientation, in this example. FIG. 5 shows measured HU values of different Teflon capsule diameters in the diagonal orientation versus different gantry rotation time, in the static condition. The differences between the HU values of the 10 mm capsule and the 2 and 1 mm capsules are 14.6% and 24.2%, respectively, for the shortest gantry rotation time of 0.35 s whereas the above differences are 13.1% and 23.1% for the longest gantry rotation time of 3.0 s.

Moving Condition

Figure 6:
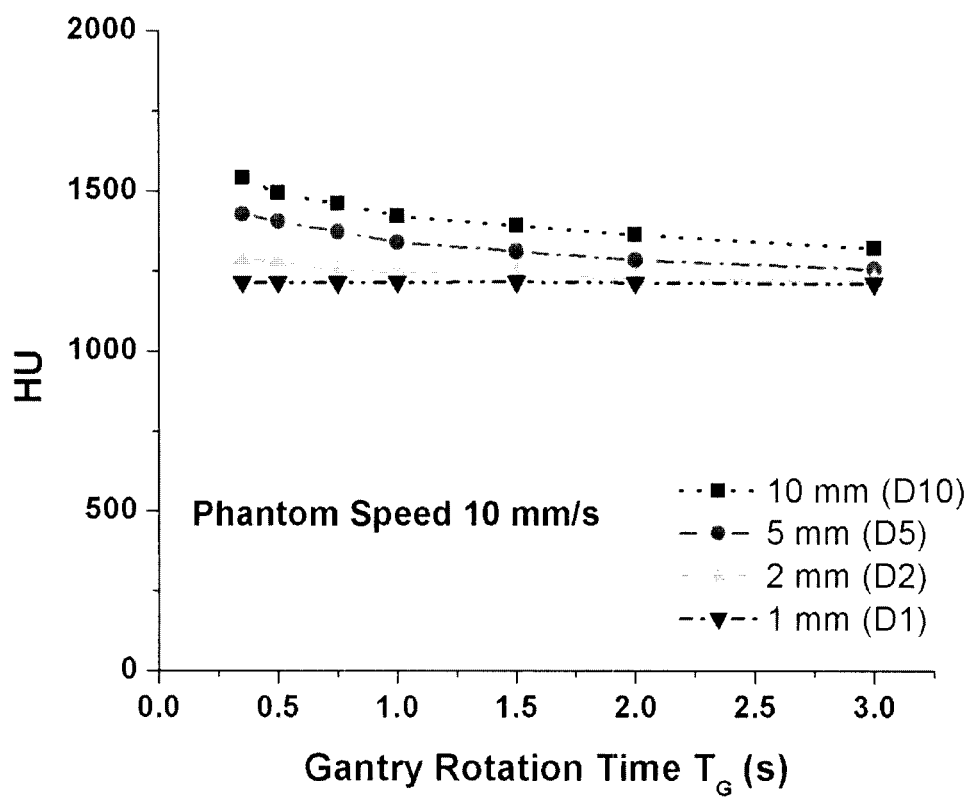
FIG. 6 shows measured HU values of different example capsules in the phantom of FIG. 1.

FIG. 6 shows HU values of different size Teflon capsules in the diagonal orientation versus gantry rotation time for a phantom speed of 10 mm/s, in this example. The discrepancies between the HU values of 10 mm capsule and 2 and 1 mm capsules were 16.5% and 21.1%, respectively, for the shortest gantry rotation time of 0.35 s whereas the above differences were 7.4% and 8.2% for the longest gantry rotation time of 3.0 s.

Figure 7:
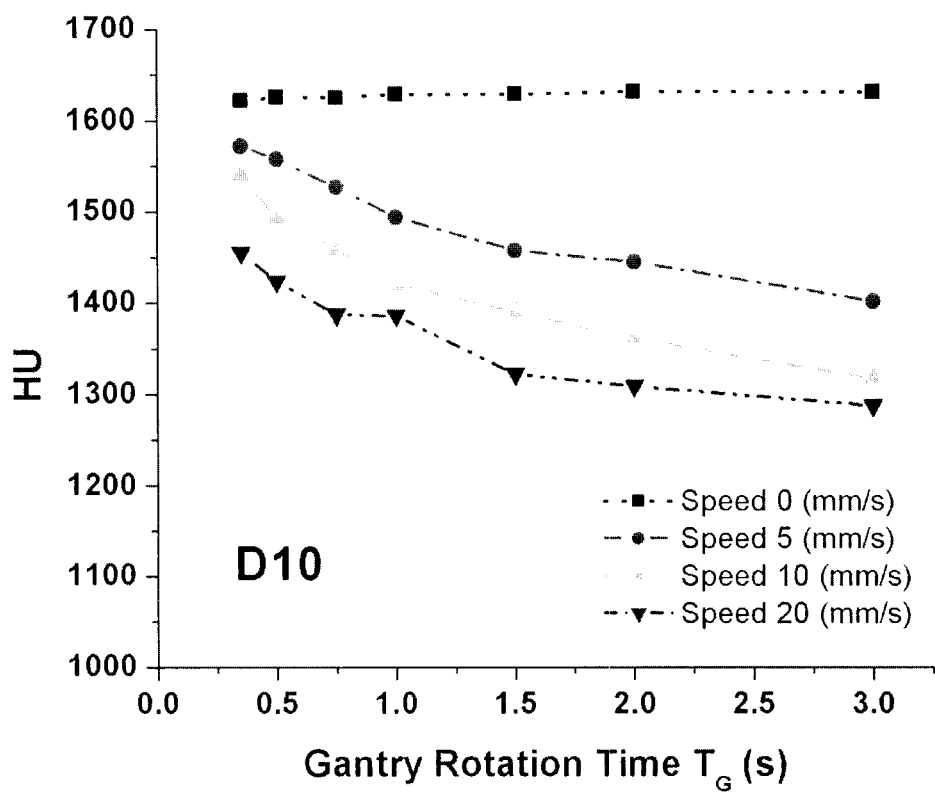
FIG. 7 shows measured HU values of an example capsule in the phantom of FIG. 1 over different rotation times.

FIG. 7 shows the HU values of the 10 mm diagonally oriented capsule versus different $T_G$ for all phantom speeds, in this example. For a given phantom motion speed, HU decreased with increasing $T_G$, as before. Increasing the phantom motion speed from 0 to 2.0 cm/s reduced the HU by 10% for $T_G$=0.35 s and by 21% for $T_G$=3 s. Measured HU values also decreased with increasing $T_G$ for the other capsule orientations, however, it was least pronounced for the longitudinal orientation (result not shown).

Figure 8:
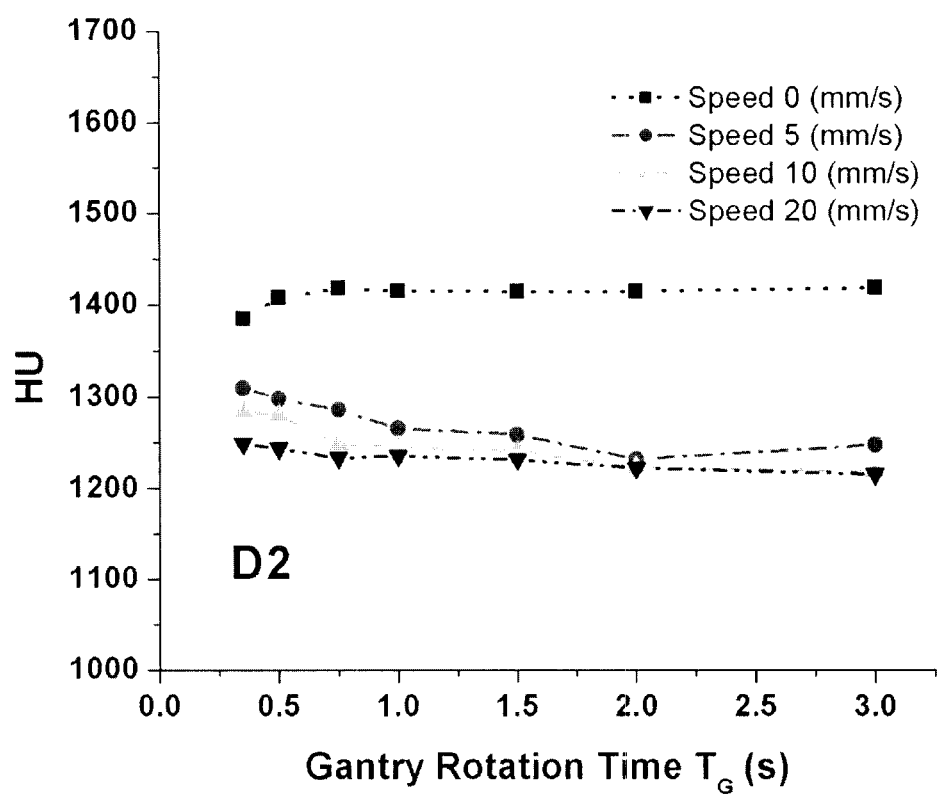
FIG. 8 shows measured HU values of another example capsule in the phantom of FIG. 1 over different rotation times.

The change in HU values versus different $T_G$ for 2 mm diagonally oriented capsules, in this example, is shown in FIG. 8. As the phantom motion speed increased from 0 to 2.0 cm/s the HU value declined by 9% for $T_G$=0.35 s and by 14% for $T_G$=3 s.

Figure 9:
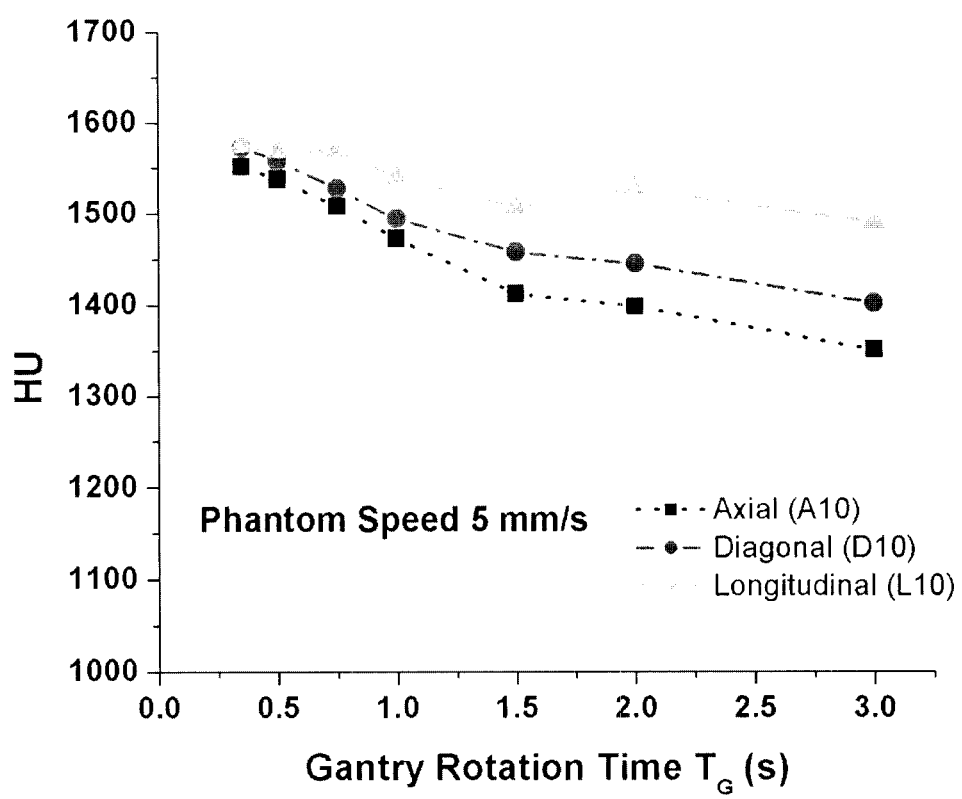
FIG. 9 shows measured HU values of example capsules in the phantom of FIG. 1 over different rotation times.
Figure 10:
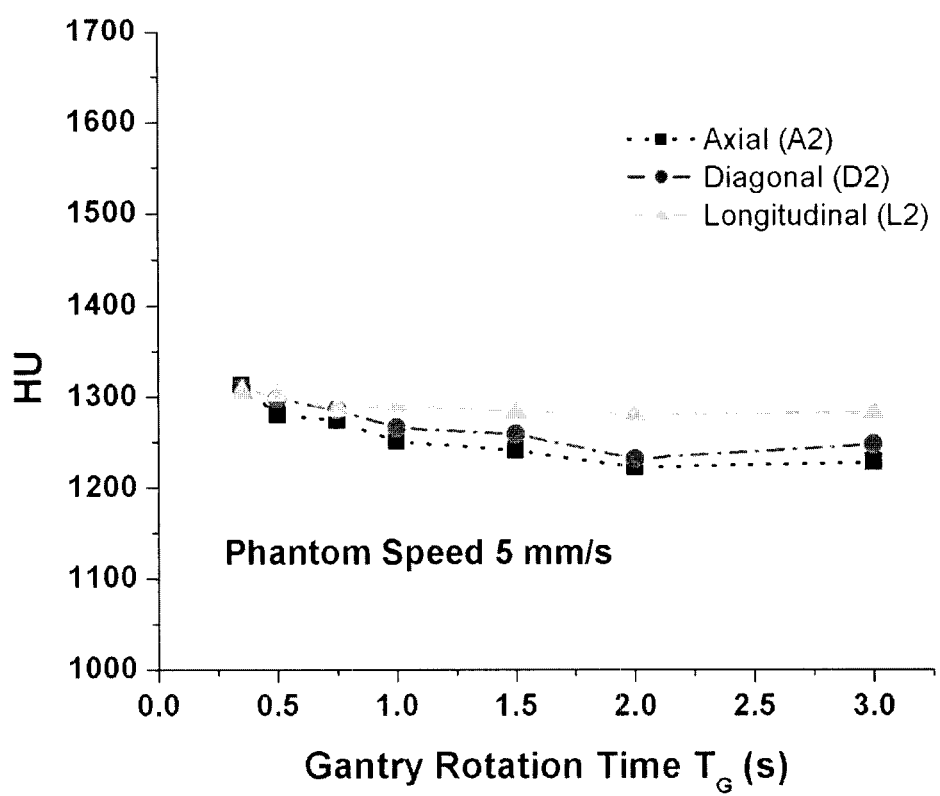
FIG. 10 shows measured HU values of example capsules in the phantom of FIG. 1 over different rotation times.

The susceptibility of vessel orientation to motion is illustrated in FIGS. 9 and 10, which shows the measured HU values of the axial, diagonal and longitudinal 10 mm and 2 mm diameter Teflon capsules versus different $T_G$ for a phantom speed of 5 mm/s, in this example. According to FIG. 9 which shows the results of the 10 mm diameter capsules the discrepancy between longitudinal and axial orientation was only 2% for $T_G$=0.35 s but 9% for $T_G$=3 s. These differences were smaller for smaller capsules, as shown in FIG. 10, where the measured HU values for $T_G$=0.35 s were within 0.5% and between 4.3% for $T_G$=3 s.

Prediction of Capsule Contrast

Figure 11:
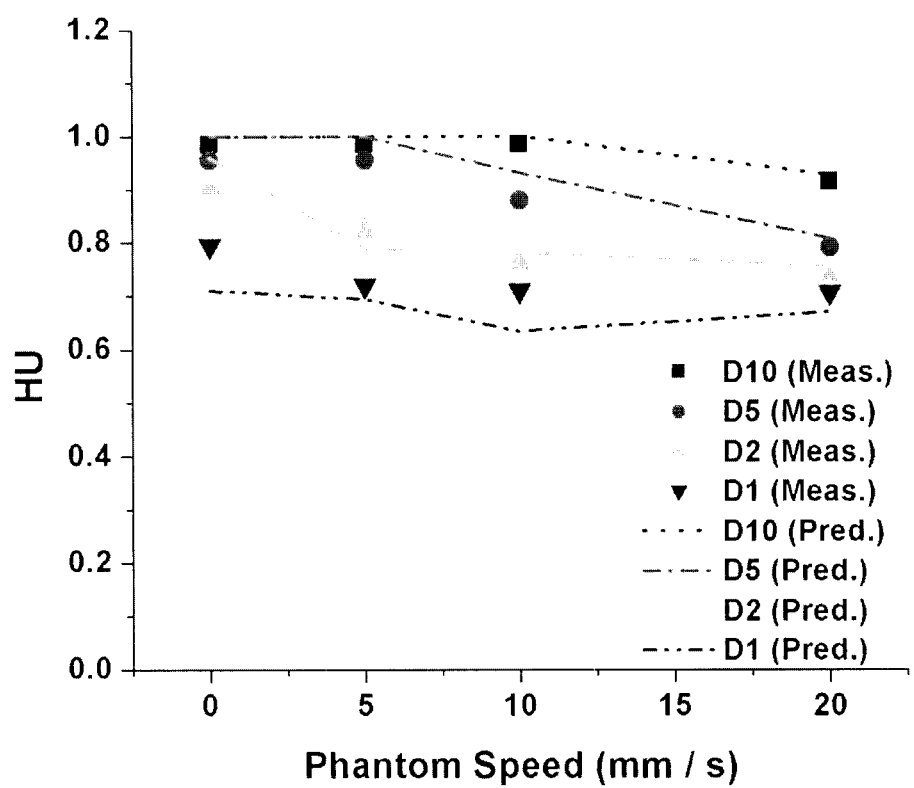
FIG. 11 shows measured and predicted maximum HU values using a motion model for the phantom of FIG. 1.

FIG. 11 shows, for the static and the moving condition, the predicted (in this example, using the motion model described above) and measured maximum HU values $HU_{max}^{mov}$ for all capsules in the diagonal orientation as a function of phantom motion speed and fixed gantry rotation time of 1 s. All values are normalized to the maximum HU value of D10 (diagonal orientation, 10 mm capsule diameter) in the static mode.

With no phantom motion, the model predicted the partial volume effect well for all capsule diameters. The partial volume effect reduced the HU value of the 1 mm capsule by 21% compared to the largest capsule and by 10% and 5% for the 2 mm and 5 mm capsules, respectively.

For the moving condition, the $HU_{max}^{mov}$ values were further decreased with increasing phantom speed. The differences between predicted HU values and the measured results in both static and dynamic condition were within 2% for largest capsules (10 mm) and within 12% for the smallest capsules (1 mm).

Discussion of Imaging Example

There are challenges in employing contrast imaging, for example DCE-CT, for measurements of tissue perfusion for organs such as liver or lung. One such issue is the mitigation of organ motion to improve the temporal tracer kinetics modeling and reduce patient dose. Under the assumption that such scans will therefore be performed under free-breathing conditions in the future, it may be useful to characterize the image artifacts that are introduced by breathing motion. If, in addition, a computational model can be developed that predicts these artifacts for a given set of motion parameters then potential correction algorithms may be developed.

The disclosed phantom and examples described above may be useful for characterization and prediction of contrast enhancement of moving vessel-like objects for different gantry rotation times and phantom speeds. In the examples described, linear motion rather than periodic motion was studied in order to quantify and model worst-case conditions. All the measurements where done for different speeds of 0, 0.5, 1.0 and 2 cm/s. These speeds may represent normal breathing motion at different phases in the breathing cycle [14] [15]. In terms of the motion model, periodic motion may be simulated, for example by linearly combining the different linear motion speeds from realistic breathing traces. Other speeds may be used, for example to simulate other motions. The motion may be linear, periodic or irregular, for example.

Effect of Capsule Diameter

FIG. 4, described above, illustrates the decrease in HU values with decreasing capsule diameter in the static condition. This is a demonstration of the partial volume effect, which occurs whenever the diameter of the capsule is very small, e.g., in the order of the full-width at half-maximum (FWHM) of the PSF of the CT scanner (approximately 1.2 mm). In this case, a single voxel typically contains a mixture of multiple HU values from Teflon and the surrounding acrylic. A lower reconstruction resolution (i.e., larger image voxel size) typically increases this effect as well. In the present examples, all scans were acquired at isotropic voxel size of 0.5 mm and hence the vessel orientation showed a smaller influence on the HU value than the capsule diameter.

Motion typically is a source of blurring in conventional imaging modalities and typically leads to further decrease in contrast enhancement. This is illustrated by comparing FIG. 6, where the additional blur of the motion decreases the partial volume effect (the difference between largest and smallest capsule diameter) as compared to the static condition (FIG. 5). A possible reason for this may be that smaller capsule diameters may be relatively less affected by the motion (FIG. 8) than the larger capsule diameters (FIG. 7). The decrease of HU is typically proportional to the distance of travel w of the capsules during the time of one gantry rotation. Both increasing phantom speed and longer gantry rotation time may increase the distance of travel. This can be seen in FIG. 7 where, as an example, the HU value for $v_p=5$ mm/s and $T_G=1.5$ is very similar to the value for $v_p=10$ mm/s and $T_G=0.75$ s.

FIG. 11 shows the results of calculated and predicted maximum HU values for different example capsules diameters in the diagonal orientation. The discrepancies between predicted and measured HU values are larger for smaller capsules. A possible reason for this may be that the motion model may not account for image noise. The maximum HU value is the value in a single voxel and as such is typically subject to image noise, in particular for the smallest capsule diameter. This was similar for other capsule diameters (and orientations) and gantry rotation speeds (results not shown). Although certain example capsule diameters are discussed for the purpose of illustration, other capsule shapes, configurations and dimensions may be used, for example depending on the application.

Effect of Vessel Orientation

According to FIG. 4, in the static condition, HU values were similar for a given capsule diameter irrespective of the orientation. This may be expected as the PSF is approximately rotation invariant in space for an isotropic voxel resolution. However, this is typically not the case under moving conditions where this symmetry is typically broken in the longitudinal direction. As a result, for a given $T_G$ and therefore distance of travel w there is less decrease in the measured HU values for the longitudinal orientation than for the diagonal and axial orientations. This may be due to the fact that in the longitudinal orientation the motion vector is parallel to the longitudinal axis of the Teflon capsule. In this case the out-of-plane motion of one end of the capsule may be compensated for by the into-plane motion of the other end. The fact that the HU values for the longitudinal capsule in FIG. 9 are decreasing rather than staying constant for increasing gantry rotation times may be a consequence of the fixed region of interest analysis described above. The diameter of the spherical ROI (22.5 mm) is only larger than w for all $T_G$ smaller than 0.5 s. However, the maximum HU value stayed constant for all $T_G$ up to 3 s (result not shown). This is also confirmed in the predictions of the motion model in FIG. 11, described above, where the maximum HU value for the diagonal capsule is unchanged for distances of travel smaller than the length of the cut of the capsule along the motion direction.

The above examples demonstrate that partial volume effect and motion blurring both contribute to a general decrease of Teflon contrast enhancement with increasing travel distance of the phantom during the time of one gantry rotation. This effect may be essentially linear with travel distance of the object during the time of one gantry rotation. In the above examples, measured HU values also decreased with increasing travel distance depending on the capsule orientation, however, it was least pronounced for the longitudinal orientation. The acquisition of such a data set for a wide variety of conditions may be useful as the basis for algorithms that correct for motion artifacts in contrast imaging.

Applications

The disclosed imaging phantom may be used for applications and quality assurance procedures in imaging modalities, such as dynamic positron-emission tomography (PET) imaging. For example, the cavities may contain an imaging material suitable for PET imaging, such as a radioactive substance. Such an imaging material may be provided in a hollow capsule (e.g., a hollow teflon capsule) that may be contained in respective cavities of the phantom. For example, possible applications may include the testing of respiratory gating acquisition and reconstruction algorithms, or list-mode acquisition and reconstruction.

The imaging phantom may be used for applications and quality assurance procedures, for example in Single Photon Emission Computed Tomography (SPECT) imaging. For example, the cavities may contain an imaging material suitable for SPECT imaging, such as a radioactive substance. Such an imaging material may be provided in a hollow capsule (e.g., a hollow teflon capsule) that may be contained in respective cavities of the phantom. For example, possible applications may include image quality tests in the presence of motion.

Although the phantom has been described for use under moving conditions, it may also be useful for calibration under static conditions instead of or in addition to calibration under moving conditions. For example, while the directional configurations of the cavities has been described as corresponding to a pre-determined direction of motion, the directional configurations may be corresponding to an intended, expected or otherwise desired direction of motion without the phantom necessarily being in motion. Where there are multiple cavities in the phantom, the directional configurations may also be aligned with respect to each other, or to an axis of the phantom. Whether in a moving condition or a static condition, where there are multiple cavities, different materials may be used for capsules in different cavities, for different calibration purposes.

For example, under static conditions or moving conditions, a phantom having cavities of different sizes and/or orientations may be used for calibration of peak contrast enhancement (e.g., using higher density capsules in the cavities). This may be useful to help understand directional dependence and/or partial volume effects of the measurements.

In another example, in both moving and static conditions, where the phantom includes multiple cavities, such a configuration may allow for multiple capsules of different materials to be imaged together in the phantom. Different capsules of different densities may be useful for creating a calibration curve of contrast concentration versus signal (i.e., imaging measurement), where the contrast concentration is represented not by an actual contrast mix but by a material having a density that produces a similar contrast enhancement. This may be useful for avoiding evaporation of contrast agent over time and/or avoiding variations in concentration due to errors in mixing the contrast, for example when calibration is repeated. This example use of the phantom may be useful for providing relatively robust and prolonged quality assurance, including under static conditions.

The use of different capsules having different densities may allow for calibration using densities much higher than that of tissues (e.g., for contrast enhancement calibration based on iodine).

Where there is only one cavity defined in the phantom, it may be useful for studying a relative or maximum enhancement.

The above examples are provided for the purpose of illustration only, and may not apply to all embodiments of the present disclosure. The examples are not intended to define or limit the scope of the disclosure. Any objectives or advantages described are only for the purpose of illustration and are not intended to be limiting. Although the disclosure refers to the use of certain imaging modalities and imaging equipment, these are for the purpose of illustration only, and other imaging modalities and imaging equipment may be suitable.

REFERENCES

1. P. V. Pandharipande, G. A. K., H. Rusinek and V. S. Lee, *Perfusion imaging of the liver: current challenges and future goals*. Radiology, 2005. 234: p. 661-673.

2. K. Miles, *Computed tomography measurements of perfusion in cancer therapy, in In Vivo Imaging of Cancer Therapy*, A.F.S.a.P. Price, Editor. 2007, Humana Press Inc.: Totowa, N.J.

3. Cao, Y., et al., *Liver function after irradiation based on computed tomographic portal vein perfusion imaging*. Int J Radiat Oncol Biol Phys, 2008. 70 (1): p. 154-60.

4. S. Mori, T. O., H. Kato, R. Kishimoto, S. Kandatsu, S. Tanada and M. Endoa, *Preliminary study: Color map of hepatocellular carcinoma using dynamic contrast-enhanced 256-detector row CT*. European Journal of Radiology, 2007. 62: p. 308-310.

5. R. Wiemker, P. R., T. Blaffert, D. Sifri, O. Hay, E. Shah, R. Truyen and T. Fleiter, *Aspects of computer-aided detection (CAD) and volumetry of pulmonary nodules using multislice CT*. The British Journal of Radiology, 2005. 78: p. 46-56.

6. E. E. Stewart, X. C., J. Hadway and T. Y. Lee, *Hepatic perfusion in a tumor model using DCE-CT: an accuracy and precision study*. Phys. Med. Biol., 2008. 53: p. 4249-4267.

7. A. Kamena, F. S., C. Grieser, L. Lehmkuhla, B. Jamil, K. Wojtal, J. Ricke, M. Pech, *Dynamic perfusion CT: Optimizing the temporal resolution for the calculation of perfusion CT parameters in stroke patients*. European Journal of Radiology, 2007. 64 (1): p. 111-118.

8. C. M. Lee, T. K. L., H. J. Wang, W. H. Lee, L. K. Shen and Y. Y. Chen, *Identification of a coronary-to-bronchial-artery communication with MDCT shows the diagnostic potential of this new technology*. J. Thorac. Imaging, 2007. 22: p. 274-276.

9. P. S. Basran, I.K.a.D.P.S., *Functional CT in lung with a conventional scanner: simulations and sampling considerations*. Phys. Med. Biol., 2004. 49: p. 1755-1771.

10. C. Coolens, S. B., T. Purdie, A. Owrangi, J. Publicover, S. Bartolac and D. Jaffray, *Implementation and characterization of a 320-slice volumetric CT scanner for simulation in radiation oncology*. Med. Phys., 2009. (In Press).

11. R. Grosjean, R. M. G., B. Sauer, A. Blum, J. Hubert and J. Felbinge. *Influence of a longitudinal motion on image quality with a 64-channel CT scanner*. in *29th Annual International Conference of the IEEE EMBS*. 2007. Lyon, France.

12. H. Shirato, Y. S., K. Kitamura, R. Onimura and S. Shimizu, *Intrafractional tumor motion: lung and liver*. Seminars in Radiation Oncology, 2004. 14 (1): p. 10-18.

13. J. D. Silverman, N.S.P.a.J.H.S., *Investigation of lung nodule detectability in low-dose 320-slice computed tomography*. Med. Phys., 2009. 36 (5): p. 1700-1710.

14. B. Thorndyke, E. S., A. Koong and L. Xing, *Reducing respiratory motion artifacts in positron emission tomography through retrospective stacking*. Medical Physics, 2007. 33 (7): p. 2632-2641.

15. P. J. Keall, G. S., H. Shukla, K. M. Forster, V. Ortiz, C. W. Stevens, S. S. Vedam, R. George, T. Guerrero and R. Mohan, *Acquiring 4D thoracic CT scans using a multislice helical method*. Phys. Med. Biol., 2003. 49: p. 2053-2067.

16. Huda W, Scalzetti E M, Levin G. Technique factors and image quality as functions of patient weight at abdominal CT. *Radiology* 2000; 217:430-435.

17. Miles K A. Perfusion CT for the assessment of tumour vascularity: which protocol? *Br J Radiol* 2003; 76 Spec No 1:S36-42.

The invention claimed is:

1. An imaging phantom for contrast imaging calibration, the phantom comprising:
   a body defining a plurality of cavities, the cavities each having a directional configuration corresponding to at least one pre-determined direction of motion of the phantom; and
   at plurality of imaging capsules configured to match and be contained in respective cavities, the imaging capsules each comprising a material having an imaging contrast different from that of the body, the imaging capsules each having different densities, the different densities being selected to produce imaging contrast enhancements representative of different concentrations of a contrast agent.

2. The phantom of claim 1 wherein the directional configuration of at least one of the cavities corresponds to the at least one pre-determined direction of motion in one of: a parallel alignment, a perpendicular alignment, and a skewed alignment.

3. The phantom of claim 1 wherein at least two of the plurality of cavities have directional configurations respectively corresponding to at least two different pre-determined directions of motion of the phantom.

4. The phantom of claim 3 wherein the plurality of cavities have respective directional configurations corresponding to at least three different pre-determined directions of motion of the phantom.

5. The phantom of claim 1 wherein the cavities are equal in size.

6. The phantom of claim 1 wherein at least two of the plurality of cavities have different sizes in at least one dimension.

7. The phantom of claim 1 wherein the directional configuration of at least one of the cavities is a cylindrical configuration having a longitudinal axis, and wherein the longitudinal axis of the cylindrical configuration corresponds to the at least one pre-determined direction of motion in one of: a parallel alignment, a perpendicular alignment, and a skewed alignment.

8. An imaging phantom for contrast imaging calibration, the phantom comprising:
   a body defining at least two cavities; and
   at least two imaging capsules configured to match and be contained in respective ones of the at least two cavities, the imaging capsules comprising respective materials having an imaging contrast different from that of the body, the imaging capsules each having different densities, the different densities being selected to produce imaging contrast enhancements representative of different concentrations of a contrast agent.

9. The phantom of claim 8 wherein the cavities have at least one directional configuration corresponding to a pre-determined direction of motion of the phantom.

10. The phantom of claim 9 wherein the cavities have at least two different directional configurations corresponding to at least two different pre-determined directions of motion of the phantom.

11. The phantom of claim 10 wherein the cavities have respective directional configurations corresponding to at least three different pre-determined directions of motion of the phantom.

12. The phantom of claim 9, wherein the respective directional configurations of the cavities correspond to respective pre-determined direction of motions in one of: a parallel alignment, a perpendicular alignment, and a skewed alignment.

13. The phantom of claim 9 wherein the directional configurations of the cavities are cylindrical configurations having longitudinal axes, and wherein the longitudinal axes of the cylindrical configurations corresponds to the respective pre-determined directions of motion in one of: a parallel alignment, a perpendicular alignment, and a skewed alignment.

14. The phantom of claim 8 wherein at least two of the cavities have different sizes in at least one dimension.

15. A combination for contrast imaging calibration, the combination comprising:
   the phantom of claim 1; and
   a motion device operable for moving the phantom in the at least one pre-determined direction of motion.

16. The combination of claim 15 wherein the motion device is operable for moving the phantom in a plurality of pre-determined directions of motion, and wherein the plurality of pre-determined directions of motion defines an open or a closed motion path in three-dimensional space.

* * * * *